United States Patent [19]
> Baylis et al.

[11] 4,177,797
[45] Dec. 11, 1979

[54] ROTARY BIOPSY DEVICE AND METHOD OF USING SAME

[75] Inventors: Shelby M. Baylis, 6800 Hubbard Rd., Clarkston, Mich. 48016; Jorge S. Szauer, Pontiac, Mich.

[73] Assignee: Shelby M. Baylis, Clarkston, Mich.

[21] Appl. No.: 774,408

[22] Filed: Mar. 4, 1977

[51] Int. Cl.² .............................................. A61B 10/00
[52] U.S. Cl. .................................. 128/754; 128/310
[58] Field of Search .................... 128/2 B, 305, 310

[56] References Cited

U.S. PATENT DOCUMENTS

| | | | |
|---|---|---|---|
| 1,867,624 | 7/1932 | Hoffman | 128/2 B |
| 2,198,319 | 4/1940 | Silverman | 128/2 B |
| 2,496,111 | 1/1950 | Turkel | 128/2 B |
| 2,850,007 | 9/1958 | Lingley | 128/2 B |
| 3,630,192 | 12/1971 | Jamshidi | 128/2 B |
| 3,929,123 | 12/1975 | Jamshidi | 128/2 B |

FOREIGN PATENT DOCUMENTS 401360  2/1974  U.S.S.R. .................................. 128/2 B

*Primary Examiner*—Kyle L. Howell
*Attorney, Agent, or Firm*—Irving M. Weiner; Pamela S. Burt

[57] ABSTRACT

An improved rotary biopsy device for extracting biopsy samples and the like from specific specimen extracting locations. The device includes an elongated inner needle member used for initial penetration of the body tissue, with an outer hollow cylindrical cutting tube thereafter being slidably received over the needle member. In use, the needle member is first penetrated, by rotating same, into the desired specimen extracting location. The outer tube is then slidably disposed thereover and pushed downwardly until it also penetrates the body tissue, and both the tube and needle are simultaneously withdrawn with the sample collected interiorly of the tube.

11 Claims, 5 Drawing Figures

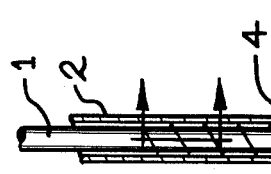
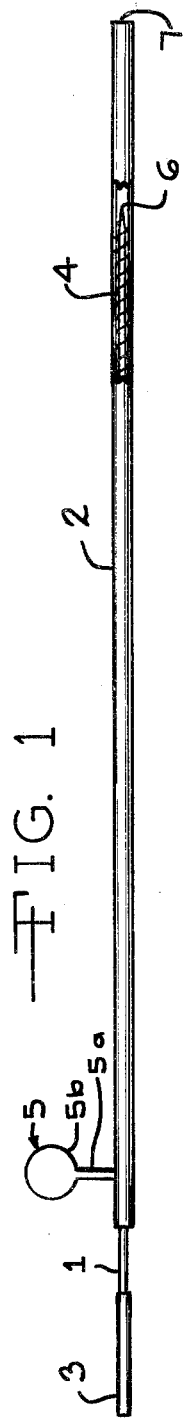
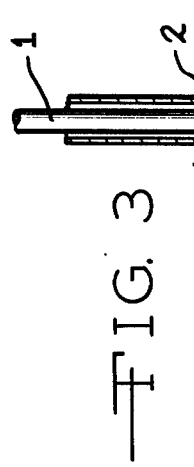
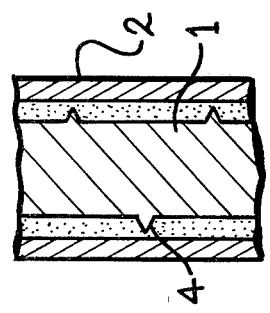
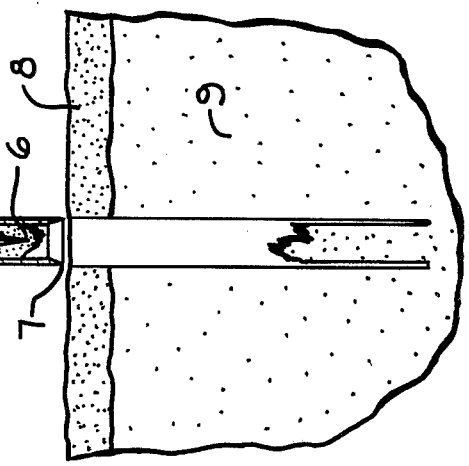
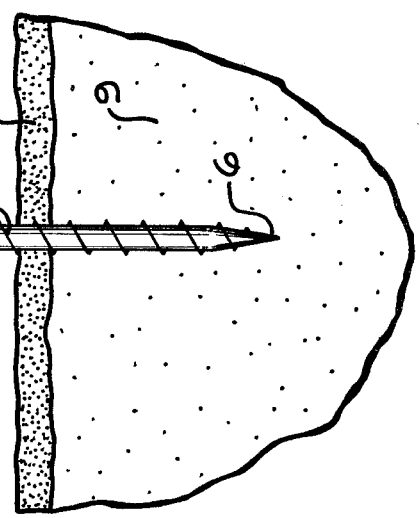

ROTARY BIOPSY DEVICE AND METHOD OF USING SAME

BACKGROUND OF THE INVENTION

1. Field of the Invention

The present invention relates generally to a device for use in connection with obtaining biopsy specimens such as, for example, from the breast, thyroid, solid tumors, bone marrow, liver, kidney, pleura, synovia, and other soft body tissue.

2. Description of the Prior Art

Prior art and conventional biopsy devices have not been successful in providing a high quality extracted specimen while at the same time minimizing trauma to the patient and providing easy removability of the specimen from the device after extraction. In particular, there has now been developed any generally acceptable biopsy device which provides the aforementioned desirable advantages and which includes a rotatable inner needle member.

Illustrative of prior art devices in the field of biopsy apparatus are those disclosed in U.S. Pat. Nos. 2,541,542; 2,919,692; 3,175,554; 3,512,519; 3,628,524; 3,683,891; 3,800,783; 3,893,445; 3,913,566; and 3,949,747. Perez U.S. Pat. No. 2,541,542 discloses a chisel-pointed needle with a cannula fitted with a small noose-like loop to cut a cylinder of tissue after the needle is removed and the cannula is pushed further into the tissue.

Ackerman U.S. Pat. No. 2,919,692 discloses an extremely thin needle for guiding a cannula to a vertebral bone surface. The needle is withdrawn, and replaced with a trephine to saw through the bone for a marrow sample.

Stewart U.S. Pat. No. 3,175,554 discloses a hollow bifurcated needle which spreads when inserted past the end of a cannula into soft tissue, and contracts when withdrawn trapping a tissue sample.

Hall U.S. Pat. No. 3,512,519 discloses a circular cutting device to be used with high-speed pneumatic rotary surgical instruments for obtaining shallow samples of the surface of skin or an organ exposed during an operation.

Jamshidi U.S. Pat. No. 3,628,524 discloses an interlocked tube and needle assembly. When the needle is removed, the biopsy sample is to expand into the tapered interior of the tube.

Eskridge U.S. Pat. No. 3,683,891 discloses a flattened section of stainless steel wire formed into a hollow helix.

Jamshidi U.S. Pat. No. 3,800,783 discloses a chisel pointed, barbed needle which serves as a penetrator for the device, and is then extended to catch a tissue sample in the barb.

Hofsess U.S. Pat. No. 3,893,445 discloses an outer hollow chisel pointed tube intended to indent a bone surface, and an inner hollow chisel pointed tube serving as a rotatable drill bit to drill through the bone marrow, and thereafter to be removed to insert prior art cannulas or hypodermic needles.

Lacey U.S. Pat. No. 3,913,556 discloses a disposable tool with a split hollow tube to make a cylindrical cut in a tissue body, and be split apart and re-inserted in the cylindrical cut to scoop out a tissue sample.

Hevesy U.S. Pat. No. 3,949,747 discloses a set of screw-together handles and screw-on tissue biopsy punches, similar in configuration to common leather punches, but much smaller. Such devices, however, have not satisfactorily provided a safe and effective biopsy instrument capable of producing high quality specimens, as is possible with the rotary biopsy device of the present invention.

SUMMARY OF THE INVENTION

The present invention provides a device for extracting biopsy samples and the like including an elongated needle member having a distal and proximal end, the distal end defining a cutting edge for initial penetration of the body tissue. The needle member has disposed along at least a portion of the length thereof body tissue cutting means. A hollow cylindrical cutting tube of substantially uniform diameter having a distal and proximal end with the distal end defining a cutting edge is also provided. The tube is adapted to be substantially tightly received over the needle member having the cutting means disposed thereon, after the needle member has been penetrated into the body tissue. The distal cutting edge of the tube projects beyond the distal cutting edge of the needle member in the body tissue when the tube is disposed over the needle member in an operative position. The needle member and the tube are adapted to be withdrawn simultaneously from the body with the tissue sample being collected interiorly of the tube.

In a preferred embodiment, the body tissue cutting means comprises a sharp helical thread disposed along a substantial portion of the length of the needle member to effect a tissue-cutting action when the needle member is rotated. The tissue sample is collected interiorly of the tube and between adjacent thread portions of the helical thread when the needle member and tube are simultaneously withdrawn from the body. Both the needle member and the tube are provided with respective handles to aid in maneuvering same, with the handle of the needle member being adapted to permit the tube to be slidably received thereover. The distal cutting edge of the tube is defined by a substantially circular beveled distal end edge of the cylindrical cutting tube. In the operative position, the proximal end of the needle member projects beyond the proximal end of the tube.

It is an object of the present invention to provide a method of utilizing the rotary biopsy device wherein the needle member is inserted into the body at a desired specimen extracting location by rotating the needle member to permit the helical thread to cut the body tissue. Thereafter, the cutting tube is slidably inserted over the needle member into the body tissue, and both the needle member and tube are finally simultaneously withdrawn from the body. The proximal end of the needle member projects beyond the proximal end of the tube and the distal cutting edge of the tube projects beyond the distal cutting edge of the needle in the body tissue when the tube has been slidably inserted over the needle into the body tissue in the operative position.

Further objects and details of the present invention will become apparent to those skilled in the art upon reading the following specification, appended claims, and the accompanying drawing.

Brief Description of the Drawings

FIG. 1 illustrates a side elevational view of the assembled biopsy device in accordance with a preferred embodiment of the present invention.

FIG. 2 depicts a front elevational view of the inner needle member as inserted into the body, with the outer tube being partially inserted thereover.

FIG. 3 depicts a front elevational view of the device in an operative position wherein the outer tube is fully inserted into the body tissue.

FIG. 4 illustrates a front elevational view of the device as the inner needle member and outer tube are being simultaneously withdrawn from the patient's body.

FIG. 5 depicts an enlarged cut-away sectional view of the specimen collected interiorly of the tube and between adjacent thread portions of the needle member.

DETAILED DESCRIPTION OF SOME PREFERRED EMBODIMENTS

There is hereby incorporated by reference thereto the entire disclosure of the aforementioned copending U.S. patent application Ser. No. 684,480.

With reference to FIG. 1, there is depicted the novel rotary biopsy device according to the present invention. The device includes an elongated solid cylindrical needle member 1 which is shown as disposed within a hollow cylindrical cutting tube 2. Both the needle 1 and the tube 2 are of uniform diameter. The needle 1 has provided on the proximal end thereof a handle 3 which is of slightly larger diameter than the needle 1, but which is of sufficiently minimal diameter to permit the tube 2, of somewhat larger diameter, to slide thereover. As can be seen in the cutaway portion of the tube 2, the needle 1 has disposed along a suitable length thereof a helical thread 4. The thread 4 has an acutely sharp cutting edge disposed along the entire length of the thread 4 to facilitate the cutting action as well as the specimen retaining action which will be described in greater detail hereinbelow. Disposed adjacent the proximal end of the tube 2 is a handle portion 5. The handle 5 is fabricated of a rod portion 5a which extends substantially perpendicular to the longitudinal axis of the tube 2 and a knob 5b secured to the end of rod 5a.

The distal end 6 of the needle 1 comprises a sharp conical needle point which permits the inital penetration of the needle 1 into the patient's body to be relatively painless with minimal trauma. The distal end 7 of the tube 2 also comprises a sharp cutting edge as will now be described with reference to FIG. 2.

Although the device as depicted in FIG. 1 illustrates the needle 1 as being disposed within the tube 2, it will now be understood with respect to FIG. 2 that initially the needle 1 and tube 2 are completely separated. To commence the specimen-obtaining procedure, the needle 1 is employed, via the sharp point 6, to initially puncture the layer of skin 8 of the patient's body. Next, to facilitate penetration of the needle 1 into the body tissue 9, the needle 1 is rotated, by rotating the handle 3 of the needle 1, in the direction of the arrow shown in FIG. 2. Upon rotation, the sharp helical thread 4 disposed along the length of needle 1 permits the needle 1 to be worked into the patient's body with minimal pain and trauma to the patient. After the needle 1 has been rotated and penetrated into the body tissue 9 to the desired position, the outer tube 2 is slidably positioned over the needle 1, and pushed downwardly towards the skin 8. In this connection, it should be noted with respect to FIGS. 1-5 that the inside diameter of the tube 2 is only slightly larger than the combined diameter of the needle 1 and the helical thread 4 disposed thereon, to just ensure a substantially tight fit between the needle 1 and the tube 2 inserted thereover. As can be seen in FIG. 2, the sharp distal cutting edge 7 of the tube 2 comprises a bevelled end edge thereof which is substantially circular in configuration. The edge 7 is extremely sharp to effect easy penetration of the tube 2 into the skin layer 8 and subsequently into the body tissue 9.

Referring now to FIG. 3, the tube 2 is illustrated as fully inserted into body tissue 9 in its operative position. The tube 2 has been pushed downwardly in the direction of the arrow shown in FIG. 3, and it should be noted that no rotational movement of the tube 2 is necessary to effect penetration, and indeed a pushing action is all that is required. In this connection, the handle 5 for the tube 2 (FIG. 1) is employed to facilitate maneuvering of the tube 2 with respect to the needle 1 and the patient's body. Also, it should be noted that as the tube 2 is pushed downwardly over the needle 1, the needle 1 remains substantially stationary, and in effect serves as a guide for the tube 2 as it is inserted. When the needle 1 and tube 2 are in the relative positions depicted in FIG. 3, the proximal end of the needle 1, including the handle 3, will be projected outwardly above the proximal end of the tube 2, as can be more clearly seen in FIG. 1. Moreover, the distal cutting edge 7 will project into the body tissue 9 outwardly of the cutting point 6 of needle 1, as depicted in FIGS. 1 and 3.

With reference now to FIG. 4, the withdrawal operation of the device will now be described. The tube 2 and needle 1 are withdrawn substantially simultaneously from the position shown in FIG. 3 to that shown in FIG. 4 in the direction of the arrow depicted in FIG. 4. In this connection, it should be noted that as the tube 2 and needle 1 are withdrawn from the patient's body no rotational movement is required. As the tube 2 and needle 1 are withdrawn, the tissue specimen will be collected interiorly of the tube 2 between the slight space provided between the inside diamter of the tube 2 and the needle 1. The major portion of the specimen will be effectively contained between adjacent thread portions of the sharp helical thread 4, and in this manner a fairly large and entirely adequate specimen size can be collected and extracted from the patient's body, with minimal pain or trauma to the patient.

Referring now to FIG. 5, an enlarged view of the obtained specimen is depicted. It can be seen that the specimen is collected in the slight space present between the inside diameter of the tube 2 and the needle 1. The thread 4 substantially aids in collecting and retaining the specimen to be extracted. Thus, the helical thread 4 serves two important functions. First, upon insertion of the needle 1 into the patient's body as described hereinabove, the sharp thread 4 serves to cut the skin and tissue during the rotational movement of the needle 1 to facilitate penetration thereof into the patient's body. Secondly, upon withdrawal of the needle 1 within the tube 2, the thread 4 functions to collect and retain the specimen sample being extracted.

After the device, with the specimen contained therein, has been fully withdrawn from the patient's body, the device may again be separated and the specimen simply and effectively removed therefrom with the use of suitable tools.

It should be noted that the needle 1 and tube 2 may be constructed of standard materials commonly used in the manufacture of surgical instruments. For example, stainless steel, polyurethane, or other suitable surgical material may be employed.

Although there have been described what are at present considered to be the preferred embodiments of the invention, it will be understood that various modifications may be made therein, and it is intended to cover in the appended claims all such modifications as fall within the true spirit and scope of the invention.

We claim:

1. A device for extracting biopsy samples and the like, comprising:
    an elongated needle member having distal and proximal ends, said distal end having a sharp conical point for penetration of the body tissue;
    said needle member having disposed along at least a portion of the length thereof body tissue helical cutting means;
    a hollow cylindrical cutting tube of substantially uniform diameter having distal and proximal ends, said distal end having a truncated conical cutting edge;
    said tube being substantially tightly slidably received over said needle member having said helical cutting means disposed thereon, after said needle member has penetrated into the body tissue;
    said distal truncated conical cutting edge of said tube projecting beyond said distal sharp conical point of said needle member in the body tissue when said tube is disposed over said needle member in an operative position; and
    said needle member and said tube being withdrawn substantially simultaneously from the body with the tissue sample being collected interiorly of said tube 2. A device in accordance with claim 1, wherein:
    said body tissue helical cutting means comprises a sharp helical thread disposed along a substantial portion of the length of said needle member to effect a tissue-cutting action when said needle member is rotated; and
    said tissue sample being collected interiorly of said cutting tube and between adjacent thread portions of said helical thread when said needle member and said cutting tube are substantially simultaneously withdrawn from the body.

3. A device in accordance with claim 2, wherein:
    said proximal end of said needle member has disposed thereon a cylindrical handle member arranged and dimensioned to permit said cutting tube to be slidably received thereover.

4. A device in accordance with claim 2, further comprising:
    a handle portion disposed on the outer surface of said cutting tube adjacent the proximal end thereof to permit said cutting tube to be maneuvered as said cutting tube is inserted over said needle member into the body tissue.

5. A device in accordance with claim 4, wherein:
    said handle portion of said cutting tube comprises a rod member extending substantially perpendicularly outward from said cutting tube and having a knob affixed thereto.

6. A device in accordance with claim 5, wherein:
    said proximal end of said needle member has a cylindrical handle member, the diameter of said handle member being predetermined to permit said cutting tube to be slidably received thereover; and
    the diameter of said cylindrical handle member is greater than the diameter of said needle member.

7. A device in accordance with claim 2, wherein:
    said distal truncated conical cutting edge of said cutting tube has a substantially circular beveled distal end edge.

8. A device in accordance with claim 3, wherein:
    said needle member is substantially longer than said cutting tube such that the proximal end of said needle member projects beyond said proximal end of said cutting tube when said device is in said operative position.

9. A method of utilizing a device for extracting biopsy samples and the like, comprising:
    an elongated needle member having distal and proximal ends, said distal end having a sharp conical point for penetration of the body tissue;
    said elongated needle member having a sharp helical thread disposed along a substantial portion of the length of said needle member to effect a tissue-cutting action when said needle member is rotated;
    a hollow cylindrical cutting tube of substantially uniform diameter having distal and proximal ends, said distal end having a truncated conical cutting edge;
    said cutting tube being substantially tightly slidably received over said needle member having said cutting means disposed thereon, after said needle member has penetrated into the body tissue;
    said distal truncated conical cutting edge of said cutting tube projecting beyond said sharp conical point of said needle member in the body tissue when said cutting tube is disposed over said needle member in an operative position; and
    said needle member and said cutting tube being withdrawn substantially simultaneously from the body with the tissue sample being collected interiorly of said cutting tube;
    comprising the steps of:
    inserting said needle member into the body at a desired specimen extracting location by rotating said needle member to permit said sharp helical thread to cut the body tissue:
    slidably inserting said cutting tube over said needle member into the body tissue; and
    substantially simultaneously withdrawing said needle member and said cutting tube from the body.

10. A method in accordance with claim 9, wherein:
    said proximal end of said needle member projects beyond said proximal end of said cutting tube, and said distal truncated conical cutting edge of said cutting tube projects beyond said distal sharp conical point of said needle member in the body tissue, when said cutting tube has been slidably inserted over said needle member into the body tissue in said operative position.

11. A biopsy device comprising:
    needle means for threaded rotary penetration into body tissue;
    said needle means including a solid cylindrical needle (1) having a sharp conical point (6) disposed symmetric to the major longitudinal axis of said solid cylindrical needle (1) for penetration into said body tissue;
    said needle means including a thread (4) disposed helically around the outer periphery of said solid cylindrical needle (1);
    said thread (4) extending from said sharp conical point (6) to a location on said solid cylindrical needle (1) which location does not penetrate said body tissue;

said thread (4) having an acutely sharp cutting edge along the entire length of said thread (4);

cutting tube means for sliding over said needle means after said needle means has penetrated into said body tissue to its furthest extent;

said cutting tube means including a hollow cylindrical tube (2) having a cutting end (7) which passes over and beyond said sharp conical point (6) and which cuts deeper into said body tissue than said sharp conical point (6);

said tube cutting end (7) being symmetric to the major longitudinal axis of said hollow cylindrical tube (2);

said tube cutting end (7) having its interior surface in the shape of a symmetric conical portion of a truncated right cone; and the interior surface of said hollow cylindrical tube (2) and adjacent thread portions of said thread (4) cooperating to collect and retain therein and therebetween a body tissue sample when said needle means and said cutting tube means are simultaneously translated to withdraw said needle means and said cutting tube means from penetration of said body tissue.

* * * * *